United States Patent [19]

Nimni

[11] Patent Number: 5,487,776
[45] Date of Patent: Jan. 30, 1996

[54] ANTI-FUNGAL NAIL LACQUER AND METHOD THEREFOR

[76] Inventor: Marcel Nimni, 2800 Neilson Way #908, Santa Monica, Calif. 90405

[21] Appl. No.: 210,220

[22] Filed: Mar. 17, 1994

[51] Int. Cl.$^6$ ...................................................... A61K 7/043
[52] U.S. Cl. ..................................... 106/18.35; 106/15.05; 106/18.32; 424/61; 514/462; 523/122
[58] Field of Search ....................... 106/3, 15.05, 18.35, 106/18.32; 514/462; 523/122; 424/61

[56] References Cited

U.S. PATENT DOCUMENTS

| | | | |
|---|---|---|---|
| 3,932,653 | 1/1976 | Stoughton | 514/423 |
| 4,039,664 | 8/1977 | Stoughton et al. | 514/462 |
| 4,557,934 | 12/1985 | Cooper | 514/399 |
| 4,957,730 | 9/1990 | Bohn et al. | 424/61 |

OTHER PUBLICATIONS

Goldman et al, "Topical Griseofulvin Therapy Of That Which Is Called *Tinea Pedis*" Acts Dermato–Venereologica, vol. 39, pp. 454–460, 1959 [No Month].
Knight, "The Activity Of Various Topical Griseofulvin . . . In The Stratum Corneum", British Journal Of Dermatology, pp. 49–55, Nov. 1973.
Aal et al, "Topically Applied Griseofulvin In The Treatment Of Superficial Dermatomycoses In Egypt", Int Med Res 5, pp. 382–386, 1977 [No Month].
Epstein, "Topically Applied Griseofulvin In Prevention And Treatment Of Trichophyton Mentagrophytes", Arch Dermatol, vol. 111, pp. 1293–1297, Oct. 1975.
Zarowny et al, "Evaluatin Of The Effectiveness Of Griseofulvin . . . Dermatophytes", Journal Of Investigative Dermatology, 64: 268–272, 1975 [No Month].
Post et al, "Topical Treatment Of Experimental Ringworm In Guinea Pigs With Griseofulvin In Dimethylsulfoxide", Can Vet. J., 20:45–48, Feb. 1979.
Wallace et al, "Topically Applied Antifungal Agents", Archives Of Dermatology, vol. 113, pp. 1539–1542, Nov. 1977.

*Primary Examiner*—Anthony Green
*Attorney, Agent, or Firm*—Poms, Smith, Lande & Rose

[57] ABSTRACT

An anti-fungal nail lacquer composition containing a film-forming agent, a solvent therefore, and an anti-fungal amount of griseofulvin which can be either in suspension or solution in the nail lacquer composition. A method of using the anti-fungal nail lacquer composition includes applying the composition to a finger or toenail and allowing the composition to remain in contact with the nail until the solvents evaporate and a thin film of griseofulvin remains on the nail.

14 Claims, No Drawings

ANTI-FUNGAL NAIL LACQUER AND METHOD THEREFOR

FIELD OF THE INVENTION

The present invention is directed to a nail lacquer containing an anti-fungal effective amount of griseofulvin. As is known in the art, nail lacquer compositions contain film-forming compounds and organic solvents. Depending on the organic solvent, the griseofulvin may be soluble or somewhat soluble at ambient temperatures in such solvent. Thus, the griseofulvin may be in solution in the nail lacquer, partially in solution and partially suspended in the nail lacquer, or be totally suspended in the nail lacquer. When the griseofulvin is partially or totally suspended in the nail lacquer, the nail lacquer should also contain a suspending agent such as bentonite.

BACKGROUND OF THE INVENTION

The fingernails and toenails are susceptible to dermatophytic infections which are caused by the invasion of fungi into the nails of human beings and other animals. There are numerous fungi, such as T. rubrum, Microsporum Canis, T. mentagrophytum, T. interdigitale, and other known fungi that can cause these types of infections. The treatment of these infections typically involves administering one or more known types of antifungal agents, e.g., griseofulvin, clotrimazole, miconazole nitrate and thiabendazole, either orally or topically depending on the particular anti-fungal agent used. While certain antifungal agents may be applied topically or orally, other antifungal agents, e.g. griseofulvin, have generally only been administered orally. Typically, griseofulvin may be administered when the dermatophytic infection has not been successfully treated with the topical application of other antifungal agents. Unfortunately this turns out to be the case with infections of the nails. The general rule is that, if not treated very early, these infections progress to become chronic and are essentially not responsive to any form of therapy, except on some occasions, to prolonged administration of orally administered griseofulvin and a few other new antifungal agents. These compounds, due to their insolubility and associated poor adsorption from the gastrointestinal tract, have to be administered in relatively large doses, for long periods of time, sometimes extending for more than one year, and have a series of undesirable side effects.

Despite the effectiveness of orally administered griseofulvin there is concern that the oral use of griseofulvin includes a risk of toxicity. It is generally believed that this risk may be reduced if griseofulvin could be successfully topically administered. The topical administration of griseofulvin has been hindered by the lack of a suitable carrier, since griseofulvin cannot be topically applied and absorbed through the dermis in its natural solid or powder state. Furthermore, griseofulvin is insoluble in water and only slightly soluble in common solvents, such as dimethylsulfoxide, dimethylformamide and acetone which are typically used as pharmaceutical carriers. The following articles which discuss the topical application of griseofulvin using various carrier systems are aimed at the skin surface rather than the nails.

"Topical griseofulvin therapy of that which is called tinea pedis", by Goldman, et al., ASMC Dermato Venerologica, line 39, page 454–460 (1959); "The activity of various topical griseofulvin preparations and the appearance of oral griseofulvin in the stratum corneum", by Knight, British Journal of Dermatology, Vol. 91, pages 49–55 (1974); "Topically applied griseofulvin in the treatment of superficial dermatomycosis in Egypt", by H. Abgel-Aal et al., Journal International Medical Research, Vol. 5, pages 382–286 (1977); "Topically applied griseofulvin in prevention and treatment of Trichophyton mentagrophytes" by Epstein et al., Archives of Dermatology, Vol. 111, pages 1293–1296 (October 1975); "Evaluation of the effectiveness of griseofulvin, tolnaftate, and placebo in the topical therapy of superficial dermatophytoses" by Zarowny et al., The Journal of Investigative Dermatology, Vol. 64 pages 268–272 (1975); "Topical treatment of experimental ringworm in guinea pigs with griseofulvin in dimethylfoxide" by Post and Saunders, Canadian Veterinary Journal, Vol. 20, pages 45–48 (February 1979); "Topically applied antifungal agents" by Wallace et al., Archives of Dermatology, Vol. 113, pages 1539–1542 (November 1977).

The carrier systems discussed by these articles may be generally classified as consisting of highly volatile solvents, (e.g., having a boiling point less than about 100° C.), oily solvents or ointments. Some of these carrier systems were found to be ineffective, or if at least partially effective, exhibited other drawbacks. Generally, the highly volatile solvents, e.g., acetone, dissipated before sufficient time had elapsed for the griseofulvin to be absorbed through the dermis, leaving a residue of griseofulvin powder on the surface. The oily solvents or ointment carriers, even when demonstrated as potentially effective as carriers, typically were applied in relatively excessive amounts leaving an oily residue even after the lapse of an extended period of time.

Topical griseofulvin compositions are also disclosed in U.S. Pat. No. 3,899,578, issued to Bird, et al., Aug. 12, 1975. The disclosed compositions are comprised of griseofulvin dissolved in various high boiling, volatile solvents, e.g., propylene carbonate, dimethylphthalate, 3 phenoxypropanol, 4-chlorophenoxyethanol, phenoxyethanol, phenylethanol, eugenol and benzyl alcohol. Benzyl alcohol in combination with dimethyl phthalate, propylene carbonate or eugenol are disclosed as preferred solvent carriers. The composition may be diluted with ethanol, n-propanol, isopropanol, propylene glycol or glycerol. However, the disclosed compositions would be generally classified as a gel, ointment or paste due to the large amount of the low volatile solvent used in their preparation. Thus, these compositions will leave an oily residue for a considerable amount of time after application. It is believed that griseofulvin is solubilized in the oily layer of the composition and will rub off on the clothing or upon washing and thus will not be absorbed to any great extent by the skin.

U.S. Pat. No. 4,820,724 also discloses a griseofulvin composition for topical application to the skin. The solvent carrier system disclosed in this patent is a mixture of a fugitive solvent having a boiling point of less than 110° C. and a delivery solvent having a boiling point of greater than 120° C. The delivery systems described in this patent are effective in promoting the absorption of griseofulvin through the skin; however, the delivery systems are easy to remove accidentally and therefore are not convenient to use.

Various compositions for application to or treatment of nails are known including nail polishes, nail polish removers, nail oil emulsions, and the like have been developed. U.S. Patent No. 3,382,151 describes an aqueous-based, formaldehyde-containing composition which can be applied to fingernails to strengthen them against cracking and splitting. The patent further discloses that the product possesses aseptic properties, curing some inflammation of the matrix of the nail and killing fungi which occasionally infect nails.

U.S. Pat. No. 4,250,164 describes a nail polish composition, which has added thereto an anti-psoriasis effective amount of a topical steroid effective against psoriasis. U.S. Pat. No. 2,799,613 describes the use of dibromopentachlorocyclohexane as a topical fungicide and bactericide and also discloses including it as an ingredient of nail polish. Certain oil-containing compositions have been disclosed as being useful as nail and cuticle conditioners or softeners. U.S. Pat. No. 2,765,257, for example, indicates that sulfonated mineral oil acts as an effective cuticle softener; while sulfonated animal and vegetable oils are not effective. Other prior art e.g., U.S. Pat. No. 4,286,609, has disclosed the soaking of fingertips in a hot, aqueous emulsion of vegetable and animal oils to moisturize, smooth and soften the surface of the nails and the tissue surrounding the nails.

U.S. Pat. No. 4,810,498 refers to nail oil composition consisting of a cosmetic oil containing jojoba oil and tolnaftate. This substance is prescribed to treat fungal infections in nails, particular sculptured nails, known for their propensity to become contaminated. This type of formulation, although potentially effective if applied frequently has the difficulty that it has an oily texture which will only display its properties while present on the nail, and is easily removed by rubbing or when hands are washed with detergents.

U.S. Pat. No. 4,957,730 described a nail varnish comprising a water insoluble film forming substance and a series of antimycotic compounds derived from a 1-hydroxy-2-pyridone structure.

There thus remains a need for a topically applied solvent carrier system which does not cause irritation or leaves a substantially large oily residue or which is easily removed. In contrast, the present invention provides a method and composition for application of griseofulvin to the nail surface, which will adhere tenaciously and yet continue to deliver the active antifungal compound (griseofulvin) into and through the nail.

SUMMARY OF THE INVENTION

The present invention is predicated upon the surprising discovery that when griseofulvin is added to a nail lacquer and the nail lacquer is applied to the toenails and/or fingernails, the griseofulvin is effective in preventing and/or alleviating dermatophytic infections of the nails to which the anti-fungal nail lacquer is applied.

Generally speaking, the nail lacquer of the present invention includes, at a minimum, an organic film former which is in solution in a solvent system of one or more biocompatible organic solvents which, upon application to the nails, evaporate, leaving a relatively hard water permeable film. Both film-forming compounds and solvent systems therefor are well known in the art and no detailed exemplification thereof is deemed necessary. For example, it is known that the film-forming compounds are those which form a film which is relatively hard and strong, such film-forming compounds including polymers and copolymers of vinyl acetate, polymers and copolymers of acrylic or methacrylic acid (e.g., polymethyl methacrylate) polyvinylacytel and polyvinylbutyrals. A particular preferred film-forming compound is nitrocellulose, either alone or in combination with one or more of the other film-forming compounds mentioned above.

Physiologically acceptable solvent systems, which will dissolve the film-forming compounds mentioned above, are known in the art and include either alone or in combination lower alkyl alcohols such as ethyl, butyl and isopropyl alcohols, aromatic solvents such as benzyl alcohol, and butyl, ethyl, and amyl acetate. As is known in the art, the solvent system preferably contains a combination of organic solvents, at least one of the organic solvents having a boiling point of below about 100° C. (e.g., between 40° C. or 50° C. and 100° C.) and at least one organic solvent having a boiling point above 100° C. (e.g. 110° C. –200° C.).

Generally, nail lacquer compositions also include a plasticizer to render the film more elastic. Plasticizers are also generally known in the cosmetic art and includes camphor, dibutyldioctyl and diphenyl phthalate and tricresyl and triphenyl phosphate.

Other ingredients of the nail lacquer include, if desired, colorants and pigments such as titanium oxide, mica, bismuth oxychloride, etc. If insoluble colorants and pigments are used, then a suspending agent such as bentonite should also be in the nail lacquer composition in order to prevent settling out of such insoluble colorants and pigments.

The amount of solvent in the nail lacquer composition of the present invention should, of course, be sufficient to solubilize and dissolve the film-forming compounds. Generally speaking, the amount of film-forming compound, relative to the organic solvent system, is relatively small. For example, the weight rate of film former to organic solvent will range from 1:3 to 1:10. The film-forming solution (i.e., the film former and organic solvent system) will in general be present in the nail lacquer composition in an amount ranging from 70 to 99.5 weight percent.

If a plasticizer is added to the nail lacquer compositions of the present invention, the amount thereof will be relatively minor compared to the amount of film former. Generally speaking, the weight ratio of film-forming compound to plasticizer will be between about 5:1 to 20:1.

A suspending agent should also be present in the nail composition if an insoluble colorant or pigment is used and, in addition, if griseofulvin is present in an amount greater than that which is dissolved in the organic solvents of the nail lacquer composition. The amount of suspending agent is not critical and will generally be present in amounts of from 1 to 10 weight percent.

The amount of griseofulvin in the nail lacquer compositions of the present invention is generally between about 0.5 weight percent and 10 weight percent with a preferred amount being between about 2 weight percent and 8 weight percent with a most preferred amount being between about 2 weight percent and 5 weight percent. Generally, if the griseofulvin is present in an amount of between about 1.5 or 2 weight percent and 3 weight percent, the remaining portion of the griseofulvin is undissolved and suspended in the nail lacquer composition. As noted, in that event, a suspending agent such as an organic clay (e.g., bentonite) is added, which allows the griseofulvin to remain in the nail lacquer composition as a colloidal suspension.

It is generally preferred that a portion of the griseofulvin be in solution and a portion of the griseofulvin be in suspension. Generally speaking, between about 25 weight percent and 75 weight percent of the total amount of griseofulvin will be in solution and between about 75 weight percent and 25 weight percent of the total amount of griseofulvin be in suspension. However, all of the griseofulvin may be in suspension or all of the griseofulvin may be in solution. What has been established, based on in vitro studies performed in my laboratories, is that the griseofulvin leaches out of the filter paper discs, impregnated with the lacquer and allowed to dry, when placed on culture dishes containing T. Mentagrophytes, a fungus responsible for many nail infections, caused significant or total inhibition of fungal growth, depending on whether one or four discs were applied to the surface of the culture plate. Patients with long-standing nail infections have benefited significantly or have been cured by the use of this formulation. In a specific embodiment, the invention is directed to a composition which is comprised of at least 0.1 weight percent griseofulvin in a clear lacquer which is essentially similar in composition to that used to manicure nails. This composition can be topically applied to the infected sites (nails and surrounding tissue) which exhibits signs of fungal infection. The invention is further directed to methods of making and using the composition, considering that the drug remains in solution and/or suspension for prolonged periods of time.

Once the griseofulvin containing lacquer is applied to the nail it rapidly hardens and forms a water permeable film containing the griseofulvin following the evaporation of the solvent system. This not only concentrates the griseofulvin at or near the site where it is needed, but it is believed facilitates the transport of the active compound through the patient's nail. Thus not only does the nail lacquer composition of this invention provide a means for applying a concentrated amount of an active compound but also promotes transport of the compound through the nail. It should be noted that the above discussion concerning the mechanism of absorption is merely a theory based on observed facts and should not be taken in any manner to limit the scope of the invention.

The nail lacquer composition may be prepared by admixing the solvents, film former and active compound in a suitable manner which assures the solubilization and/or suspension of the griseofulvin in the solvents. Furthermore, the composition may be applied to the affected area by any suitable means.

There are various types of dermatophytic infections which this composition of the invention may be used to treat. Generally, this composition may be used to treat the various dermatophytid infections, and nail infections caused by fungi (Onychomycosis). These types of infections may be caused by numerous fungi, e.g., those classified under the genera: trichophyton, microsporum or epidermophyton.

PREFERRED EMBODIMENT

The antifungal agent griseofulvin used to treat fungal infections in accordance with this embodiment of the invention is represented by the following general formula:

| Compound | Parts by Weight |
| --- | --- |
| Nitrocellulose | 15 |
| Ethyl Acetate | 19 |
| n-Butyl Acetate | 19 |
| Isopropyl Alcohol | 29 |
| Acetate Triethyl Citrate | 6 |
| Polyester Resin | 6 |
| Camphor | 2 |
| Stealkonium Hectorite (bentonite) | 2 |
| Silica | tr. |

After this solution which contains a suspension base consisting of Stealkonium Hectorite with small amounts of silica is prepared, 4 wt. % of griseofulvin is added, and mixed with a variable speed laboratory stirrer. Approximately 1.5% of griseofulvin is in true solution and 2.5% remains in colloidal suspension aided by the organo clay molecules of the bentonite.

The resulting composition is topically applied directly to the infected site. After application the solvents quickly dissipate by evaporation, due to the body temperature of the patient, leaving as a residue a thin water soluble film on the affected area.

The composition may be applied to the affected area by any satisfactory means, such as a small brush, cotton swab or spatula, being the most satisfactory. The effective amount of the composition applied to the infected area is such to provide a thin layer of the residue after evaporation of the solvents. The precise amount of the composition is not critical, however, excessive application will not be beneficial. Removal of the lacquer should be accomplished periodically by using a suitable solvent (usually every 2–4 days). This could be achieved with any nail polish remover available commercially, or preferably a mixture of acetone-plant or animal tissue oil (9:1) containing 1% griseofulvin in solution. This maintains the levels of drug in the tissue and the oil prevents the nails from becoming brittle, a problem which is particularly prevalent in individuals suffering from such infections.

The utilization of this composition ensures that the griseofulvin remains in the lacquer for a sufficient enough time on the patient's nail to allow for absorption of the griseofulvin. Furthermore, the topical application of griseofulvin using this composition allows a several order of magnitude reduction in the amount of griseofulvin given the patient in comparison with oral administration. This reduces the potential risks associated with the oral administration of griseofulvin as discussed above and the potential of skin irritation caused by the solvent.

While the preferred embodiments have been described, various modifications and substitutions may be made thereto without departing from the spirit and scope of this invention. Accordingly, it is to be understood that the present invention has been described by way of illustration and not limitation.

I claim:

1. An anti-fungal nail lacquer composition consisting essentially of an organic film former in solution in an organic solvent system therefor, a suspending agent, and an anti-fungal effective amount of griseofulvin, said organic film former forming a water permeable film containing the griseofulvin when the organic solvent system evaporates, wherein a portion of the griseofulvin is in solution and a portion of the griseofulvin is present as a colloidal suspension.

2. An anti-fungal nail lacquer composition according to claim 1 wherein the weight ratio of film former to organic solvent is from 1:3 to 1:10.

3. The anti-fungal nail lacquer composition according to claim 2 wherein the amount of griseofulvin is from 0.5 weight percent to 10 weight percent and the combined amount of film former and organic solvent is from about 70 weight percent to 99.5 weight percent.

4. A nail lacquer composition according to claim 1 wherein the total amount of griseofulvin present in said composition is as a colloidal suspension.

5. A nail lacquer composition according to claim 1 wherein 25 weight percent to 75 weight percent of the total amount of griseofulvin is present as a colloidal suspension.

6. A nail lacquer composition according to claim 1 wherein the suspending agent is bentonite.

7. A nail lacquer composition according to claim 1 wherein said film former is nitrocellulose.

8. A method for treating dermatophytic infections of the nails of animals, which comprises applying to said nails an anti-fungal amount of a nail lacquer composition consisting essentially of a film former in an organic solvent system therefor, a suspending agent, and an anti-fungal effective amount of griseofulvin, wherein a portion of the griseofulvin is in solution and a portion of the griseofulvin is present as a colloidal suspension in said nail lacquer composition, and allowing said nail lacquer composition to remain on said nail until a sufficient amount of organic solvent has evaporated, leaving a water permeable film of film-former and griseofulvin on said nail.

9. A method according to claim 8 wherein the weight ratio of film-former to organic solvent is from 1:3 to 1:10 in said nail lacquer composition.

10. A method according to claim 9 wherein the amount of griseofulvin is from 0:5 weight percent to 10 weight percent and the combined amount of film former and organic solvent is from 70 weight percent to 99.5 weight percent in said nail lacquer composition.

11. A nail lacquer composition according to claim 8 wherein the total amount of griseofulvin present in said nail lacquer composition is as a colloidal suspension.

12. A method according to claim 8 wherein 25 weight percent to 75 weight percent of the total amount of griseofulvin is present in said nail lacquer composition as a colloidal suspension.

13. A method according to claim 8 wherein the suspending agent is bentonite.

14. A method according to claim 8 wherein said film-former is nitrocellulose.

* * * * *